(12) United States Patent
bt. Abang Masli et al.

(10) Patent No.: US 8,017,837 B2
(45) Date of Patent: Sep. 13, 2011

(54) METHOD FOR PRODUCING TRANSGENIC PLANTS

(75) Inventors: Dayang Izawati bt. Abang Masli, Kajang (MY); Ahmad Parveez Ghulam Kadir, Kajang (MY); Abdul Masani Mat Yunus, Kajang (MY)

(73) Assignee: Malaysian Palm Oil Board, Kajang (MY)

( * ) Notice: Subject to any disclaimer, the term of this patent is extended or adjusted under 35 U.S.C. 154(b) by 455 days.

(21) Appl. No.: 12/178,225

(22) Filed: Jul. 23, 2008

(65) Prior Publication Data
US 2009/0038032 A1    Feb. 5, 2009

(30) Foreign Application Priority Data
Jul. 30, 2007  (MY) ............................... PI 20071240

(51) Int. Cl.
*C12N 15/84* (2006.01)
*C12N 15/82* (2006.01)
*A01H 4/00* (2006.01)

(52) U.S. Cl. ........ 800/294; 800/293; 800/281; 800/288; 800/300; 435/469; 435/470; 435/430.1; 435/431

(58) Field of Classification Search ........................ None
See application file for complete search history.

(56) References Cited

U.S. PATENT DOCUMENTS
7,807,866 B2 * 10/2010 Ghulam Kadir ............. 800/278

OTHER PUBLICATIONS

Parveez et al. Biochemical Society Transactions 28(6): 969-972 (Dec. 2000).*
Nandadeva et al. Plant Cell Reports 18(6): 500-504 (Feb. 1999).*
Uze et al. Plant Science 130(1): 87-95 (Dec. 1997).*
Scorza et al. Plant Cell Reports 14(9): 589-592 (1995).*
Perl et al. Nature Biotechnology 14(5): 624-628 (May 1996).*

* cited by examiner

*Primary Examiner* — David T Fox
(74) *Attorney, Agent, or Firm* — Workman Nydegger

(57) ABSTRACT

A method for producing transgenic plants, including treating a target tissue using plasmolyzing media (PM) which contains 4% to 10% of sucrose and 100 μM to 300 μM of Acetosyringone (AS) and gold particles. The target tissue is infected by a bacterial suspension using a suitable strain and a suitable transformation vector. A PM containing 4% to 10% sucrose and 100 μM to 300 μM AS is treated for a period between 1 to 3 days. Cultivation is performed in a cultivation media in a dark condition at a temperature between 25° C. to 30° C. A non-selection media with an antibiotic is introduced. A selection media containing an active ingredient phosphinothricin (PPT) is introduced in a light condition at a temperature of between 25° C. to 30° C. in a sub culture for a period of between 3 weeks to 1 month. The putative transformant is regenerated and the number of copies of the transgenes is analyzed.

21 Claims, No Drawings

METHOD FOR PRODUCING TRANSGENIC PLANTS

FIELD OF INVENTION

The present invention relates to a method for producing transgenic plants.

BACKGROUND OF INVENTION

Oil palm (*Elaeis guineensis* Jacq.) is one of the most important economic crops for Malaysia. In year 2002, plantation area for oil palm covers around 3.7 million hectares. Apart from that, Malaysia is the world's largest producer and exporter of palm oil with a 50% share of world's palm oil production and 61% share of exports (Chang et al., 2003).

*Agrobacterium tumefaciens* is one of nature's most successful organisms for genetically engineering plants and is routinely used to transfer desirable genes into dicotyledon plants. *Agrobacterium*-mediated transformation are relatively efficient and a low copy number of intact, non-rearranged transgenes can be integrated into the plant genome (Gelvin, 1998). Later, successful transformation of monocotyledon plants using *Agrobacterium*-mediated transformations have been achieved (Hiei et al., 1994; Rashid et al., 1996; Ishida et al., 1996). Inefficiency of transformation of monocotyledon plant species was thought caused by lack of production of virulence inducing substances (Usami et al., 1987; Sahi et al., 1990). The development of this method to transfer the gene(s) of interest into monocot plants was thought to be a bottleneck since these plants are not the natural host for *Agrobacterium*.

The known method for transforming cells of an oil palm with genetic material to produce a genetically-modified and regenerated oil palm plant is by (i) obtaining embryogenic calli from oil palm cabbage, (ii) transforming embryogenic calli, (iii) selecting for transformed calli, (iv) maintaining transformed calli for a time and under conditions sufficient for the formation of polyembryogenic calli cultures and (v) regenerating transformed plantlets from polyembryogenic calli culutres.

Studies are ongoing to modify this monocot plant through genetic engineering to improve the quality of palm oil (Parveez et al., 1999). Previously, microprojectile bombardment was chosen as the preferred method for transformation of monocot plants (Christou, 1996).

SUMMARY OF INVENTION

Accordingly, there is provided a method for producing transgenic plants. The method includes treating a target tissue using plasmolyzing media (PM) which contains 4% to 10% of sucrose and 100 µM to 300 µM Acetosyringone (AS) and gold particles; infecting the target tissue by a bacterial suspension which contains 100 µM to 300 µM AS, having an optical density of between 0.05 nm to 0.8 nm, time of infection of between 30 minutes to 3 hours and at a temperature of between 25° C. to 30° C. using a suitable strain and a suitable transformation vector; treating in a PM which contains 4% to 10% of sucrose and 100 µM to 300 µM of AS for a period of between 1 to 3 days; cultivating in a co-cultivation media (CM) which contains 100 µM to 300 µM of AS, in a dark condition at a temperature of between 25° C. to 30° C. for a period of between 1 to 5 days; introducing a non selection media with an antibiotic in a light condition at a temperature of between 25° C. to 30° C. for a period of between 1 week to 1 month; introducing a selection media containing a herbicide containing an active ingredient phosphinothricin (PPT) in a light condition at a temperature of between 25° C. to 30° C. in a sub culture for a period of between 3 weeks to 1 month; regenerating the putative transformant; and analyzing the number of copies of the transgenes.

The present invention consists of several novel features and a combination of parts hereinafter fully described and illustrated in the accompanying description, it being understood that various changes in the details may be made without departing from the scope of the invention or sacrificing any of the advantages of the present invention.

DETAILED DESCRIPTION OF THE PREFERRED EMBODIMENTS

The present invention relates to a method for producing transgenic plants. Hereinafter, this specification will describe the present invention according to the preferred embodiments of the present invention. However, it is to be understood that limiting the description to the preferred embodiments of the invention is merely to facilitate discussion of the present invention and it is envisioned that those skilled in the art may devise various modifications and equivalents without departing from the scope of the appended claims.

The invention provides a method for producing transgenic plants and more particularly transgenic oil palm plants (*Elaeis* species). In accordance with the invention, oil palm plants expressing a gene of interest which confer particular phenotypic traits, is provided. The bar gene is a plant selectable marker gene that confers resistance to phosphinothricin (PPT), which is an active ingredients contain in herbicide known as Basta®. The gene of interest may also confer resistant to pest including a pathogenic agent or disease condition, or the genes may modify lipids and non-lipid components of palm oil resulting in improved quality of palm oil or altered or improved production of industrial oils and chemicals and/or the genes may encode nutraceutical and pharmaceutical compounds.

In the present invention, it is intended to optimize the parameters involved in *Agrobacterium*-mediated transformation and finally routinely produce transgenic oil palm via the method of the present invention.

Several approaches such as the usage of phenolic compound substance like acetosyringone, plasmolysis medium, physical injury of the target tissue and also construction of vector containing different vir genes were hoped to improve the gene delivery in oil palm by *Agrobacterium*. To engineer plant genetically and to obtain efficient stable transgenic plant, optimization of above parameters is important to be considered.

Microprojectile bombardment and sonication are effective methods for wounding or causing physical injury to promote *Agrobacterium*-mediated transformation. Wounding by bombardment yields highly efficient transformation of carnation. Compared to bombardment, sonication is a very easy and low cost method to substantially enhanced the efficiency of the transformation of low or non-susceptible plant species. The cavitation caused by sonication results in thousands of microwounds on and below the surface of plant tissue. This wounding pattern permits *Agrobacterium* to travel deeper and more completely throughout the tissue compared to conventional microscopic wounding, increasing the probability of infecting plant cells.

Phenolic plant metabolites released from damaged cells are required for the activation of virulence functions within *Agrobacterium*. Cells at the wound site initiate the synthesis of phenolic compound which are thought to be produced as antibacterial agents and were recognised by invading *Agrobacterium tumefaciens* and serve to initiate DNA transfer. Cells at the wound site undergo a few round of cells division thus helping to repair the wound site. This cells division appears to be important in increasing the efficiency with which the DNA transfer and integration takes place.

The pre-treatment by plasmolyzing is known to have produced a rapid and efficient transformation of Panax ginseng, and as in rice, 10% sucrose pre-treatment of immature embryos enhanced the frequency of *Agrobacterium*-mediated transformation.

The details of the present invention will now be described in detail.

1. Plant Material

Embryogenic calli were initiated from oil palm cabbage and was supplied from Tissue Culture Group of Malaysian Palm Oil Board (MPOB). The embryogenic calli were cultured onto embryogenic callus (EC) medium prior to transformation process.

2. Proliferation and Maintenance of Transgenic Embryogenic Calli

The transgenic calli were cultured and maintained on EC media (MS salts (Murashige and Skoog, 1962)+$Y_3$ vitamins (Eeuwans, 1976)+0.0375 g/L NaF eEDTA+0.1 g/l myo-Inositol+0.1 g/l L-glutamine+0.1 g/l L-asparagine+L-arginine+3% sucrose+5 µM α-Naphtaleneacetic acid (NAA)+0.8% agar, pH 5.7). The calli were incubated at 28° C. in the presence of light and were subcultured every 30 days into fresh medium.

Green-coloured polyembryogenic cultures were obtained after at least 4 months on the EC media. Once the polyembryogenic calli were big enough for regeneration, they were transferred into conical flask containing shoot-inducing medium to initiate shoots more effectively.

3. Plant Regeneration

The polyembryogenic cultures were subcultured continuously until large enough shoot clumps had been produced. Normally at least 3 months were needed for the first shoots to be produced from the polyembryogenic culture. The shoot clumps were then isolated and transferred into rooting media. Plantlets were incubated at 28° C. in light until roots had formed. At least two months were usually needed for roots to be produced from individually isolated shoot clumps. Once the roots were big enough, the plantlets were transferred into polybags containing soil and kept in the nursery for further growth.

4. Pre-treatment of Embryogenic Calli by Bombardment

Embryogenic calli were bombarded using Biolistic PDS/He 1000 device (BioRad Laboratories, Hercules, Calif., USA). Gold microcarriers (1.0 micrometer; BioRad) were used at a concentration of 60 mg/ml in absolute ethanol. Suspensions were vortexed vigorously for 1-2 minutes to remove aggregated lumps. This was repeated three times. The suspensions were spun for 1 minute at 10,000 rpm and the supernatant was discarded. The pellet was resuspended in 1 ml of sterile distilled water, vortexed, spun for 1 minute and the supernatant discarded. The process was repeated once. The final pellet was resuspended in 1 ml of sterile distilled water and, while continuing vortexing, 50 µl aliquots (for 4-8 bombardments) were transferred to microtubes. These aliquots were stored at 4° C. until needed.

Preparation of gold mixture and bombardment were carried out in a Class II biosafety cabinet. 50 µl of $CaCl_2$ (2.5 M) and 20 µl spermidine (0.1 M, free base form, molecular biology grade) were added one by one to the 50 µl gold particles suspension. To obtain equal coating, the addition of spermidine was carried out while the mixture was still mixing. The mixture was vortexed for 3 minutes and spun for 10 second at 10,000 rpm and the supernatant discarded. The pellet was washed with 250 µl of absolute ethanol. The final pellet was resuspended in 60 µl of absolute ethanol. An aliquot (6 µl) was loaded onto the centre of the macrocarrier and air-dried.

Approximately, 0.5-0.7 g of embryogenic calli were subcultured onto plasmolyzing media for an hour prior to bombardment with gold particles. Bombardments were carried out once at the following conditions: 1100 psi rupture disc pressure; 6 mm rupture disc to macrocarrier distance; 11 mm macrocarrier to stopping plate distance, 75 mm stopping plate to target tissue distance and 67.5 mm Hg vacuum pressure. The bombarded tissues were ready for transformation.

5. Selection of Transformed Embryogenic Calli

Selection was carried out using Basta® (13.5% PPT) at concentrations of 10 µg/ml Basta® after one month of bombardment. Selection was carried out at 28° C. in light condition.

Upon transfer to medium containing selection agents, untransformed embryogenic calli began to die and only resistant embryogenic calli proliferated. Resistant embryogenic calli began to emerge, surrounded by dark-brown dead embryogenic calli, at 6-8 weeks after exposure to the selection agent. Due to the distinct color of transformed and untransformed embryogenic calli, selection could be very conveniently carried out. The resistant embryogenic calli were further subcultured in media containing selective agent for proliferation and regeneration.

Media Compositions

Embryogenic Callus Media (EC)

MS salts (Murashige and Skoog, 1962)+$Y_3$ vitamins (Eeuwans, 1976)+0.0375 g/L NaF eEDTA+0.1 g/l myo-Inositol+0.1 g/l L-glutamine+0.1 g/l L-asparagine+L-arginine +3% sucrose+5 µM α-Naphtaleneacetic acid (NAA)+0.8% agar Bacterial Induction Media (BIM)

Same as EC media but contain no agar, with addition 200 µM Acetosyringone and sucrose was increased to 6%.

Plasmolyzing Media (PM)

Same as BIM but contain agar

Co-cultivation Media (CM)

Same as EC media but with addition of 200 µM Acetosyringone

Selection Media

Same as EC media with addition of 10 µg/ml Basta®.

Shoot Inducing Media

MS salts (Murashige and Skoog, 1962)+$Y_3$ vitamins (Eeuwans, 1976)+0.1 g/l myo-Inositol+0.1 g/l L-glutamine+0.1 g/l L-asparagine+L-arginine+0.0375 g/L NaF eEDTA+3% sucrose+0.1 µM α-Naphtaleneacetic acid (NAA)+0.8% agar Rooting Media MS salts (Murashige and Skoog, 1962)+$Y_3$ vitamins (Eeuwans, 1976)+0.0375 g/L NaF eEDTA+0.1 g/l myo-Inositol+0.3 g/l L-glutamine+6% sucrose+9 µM α-Naphtaleneacetic acid (NAA)+0.15% activated charcoal All media was adjusted to pH 5.7 prior to autoclaving (15 psi, 121° C., 20 minutes)

Parameters involved in oil palm transformation using *Agrobacterium tumefaciens*-mediated method.

| No | Parameters | Range | Preferred |
|---|---|---|---|
| 1. | Temperature for bacteria | 25-30° C. | 27° C. |
| 2. | Temperature for plant | 25-30° C. | 28° C. |
| 3. | Bacterial optical density (OD) at 600 nm | 0.05-0.8 nm | 0.2 nm |

-continued

| No | Parameters | Range | Preferred |
|---|---|---|---|
| 4. | Co-cultivation period | 1-5 days | 3 days |
| 5. | Infection period | 30 min-3 hours | 2 hour |
| 6. | Pre treatment in PM media | 30 min-3 hour | 1 hour |
| 7. | Post treatment in PM media | 1-3 days | 1 day |

The invention claimed is:

1. A method for producing transgenic oil palm, the method comprising:
    (a) treating a target tissue using plasmolyzing medium (PM) which contains 4% to 10% of sucrose and 100 µM to 300 µM of Acetosyringone (AS) and gold particles, wherein the target tissue comprises embryogenic calli from oil palm and the embryogenic calli are bombarded with the gold particles;
    (b) infecting the target tissue with a bacterial suspension of a suitable *Agrobacterium* strain that contains a suitable transformation vector comprising a transgene and 100 µM to 300 µM AS, the bacterial suspension having an optical density of between 0.05 to 0.8 nm, and the infecting being carried out for a time of between 30 minutes to 3 hours and at a temperature of between 25° C. to 30° C.;
    (c) treating the infected target tissue in a PM having 4% to 10% sucrose and 100 µM to 300 µM AS and for a period of time of between 1 to 3 days;
    (d) cultivating the infected target tissue in a co-cultivation medium (CM) that contains 100 µM to 300 µM of AS, wherein the cultivating is carried out in a dark condition at a temperature of between 25° C. to 30° C. for a period of between 1 to 5 days;
    (e) treating the infected target tissue with a non-selection medium including an antibiotic, wherein the treating is carried out under light at a temperature of between 25° C. to 30° C. for a period of between 1 week to 1 month;
    treating the transformed target tissue with a selection medium including a herbicide, the herbicide including phosphinothricin (PPT) as an active ingredient, wherein the treating is carried out under light at a temperature of between 25° C. to 30° C. and sub cultured to select for a transformant comprising the transgene;
    (g) regenerating the putative transformant comprising the transgene; and
    (h) analysing the number of copies of the transgenes.

2. A method as claimed in claim 1, wherein the PM in step (a) contains 6% sucrose.

3. A method as claimed in claim 1, wherein the PM in step (a) contains 200 µM AS.

4. A method as claimed in claim 1, wherein the gold particles are bombarded into the target tissue in step (a) to cause physical injuries to the target tissue.

5. A method as claimed in claim 1, wherein the bacterial suspension in step (b) contains 200 µM AS.

6. A method as claimed in claim 1, wherein the bacterial suspension in step (b) has an optical density of 0.05-0.8 at 600 nm.

7. A method as claimed in claim 1, wherein the infecting of step (b) is carried out for a period of 30 minutes to 3 hours.

8. A method as claimed in claim 1, wherein the infecting of step (b) is carried out at a temperature of between 25° C. to 30° C.

9. A method as claimed in claim 1, wherein the strain in step (b) is *Agrobacterium tumefaciens*, LBA 4404.

10. A method as claimed in claim 1, wherein the transformation vector in step (b) is a plasmid comprising a bar gene.

11. A method as claimed in claim 1, wherein the PM in step (c) contains 6% sucrose.

12. A method as claimed in claim 1, wherein the PM in step (c) contains 200 µM AS.

13. A method as claimed in claim 1, wherein step (c) is conducted for 1 day.

14. A method as claimed in claim 1, wherein the CM in step (d) contains 200 µM AS.

15. A method as claimed in claim 1, wherein step (d) is conducted at a temperature of 27° C.

16. A method as claimed in claim 1, wherein step (d) is conducted for 3 days.

17. A method as claimed in claim 1, wherein step (e) is conducted at a temperature of 28° C.

18. A method as claimed in claim 1, wherein step (e) is conducted for 1 month.

19. A method as claimed in claim 1, wherein step (f) is conducted at a temperature of 28° C.

20. A method as claimed in claim 1, wherein step (f) is conducted every 1 month.

21. A method as claimed in claim 1, wherein the analysing of the number of copies is conducted using PCR, Dot Blot, Southern Blot, or Leaf Painting.

* * * * *

UNITED STATES PATENT AND TRADEMARK OFFICE
CERTIFICATE OF CORRECTION

PATENT NO. : 8,017,837 B2  
APPLICATION NO. : 12/178225  
DATED : September 13, 2011  
INVENTOR(S) : bt. Abang Masli et al.

Page 1 of 1

It is certified that error appears in the above-identified patent and that said Letters Patent is hereby corrected as shown below:

Column 2
Line 31, change "ingredients contain in" to --ingredient contained in--
Line 56, change "enhanced" to --enhance--

Column 3
Line 3, change "round of cells" to --rounds of cell--
Line 4, change "cells" to --cell--
Line 33, change "into conical" to --into a conical--

Column 4
Line 1, change "10 second" to --10 seconds--

Column 5
Line 37, before "treating" insert --(f)--

Signed and Sealed this
Seventeenth Day of January, 2012

David J. Kappos
*Director of the United States Patent and Trademark Office*